United States Patent Office

Re. 24,287
Reissued Mar. 12, 1957

24,287

DIBASIC ACID ESTERS OF GLYCOLS

Paul V. Smith, Jr., Sunningdale, England, assignor to Esso Research and Engineering Company, a corporation of Delaware No Drawing. Original No. 2,703,811, dated March 8, 1955, Serial No. 52,429, October 1, 1948. Application for reissue November 19, 1956, Serial No. 623,269

8 Claims. (Cl. 260—485)

Matter enclosed in heavy brackets [ ] appears in the original patent but forms no part of this reissue specification; matter printed in italics indicates the additions made by reissue.

This invention relates to a new class of compounds which have been found to be particularly suitable for use as synthetic lubricants because of their low pour points and high viscosity indices.

In the lubricant art, considerable progress has been realized in recent years in the production of lubricants characterized by one or more specific properties and adapted for particular uses. In the main, this progress can be attributed to two developments: the first, new refining procedures, and the second, addition agents capable of imparting particular properties to available lubricants. Thus, viscosity index improvers and pour depressants are added to automotive lubricants to render the lubricants more adaptable to wide changes in temperature conditions, while other agents are added to improve the load-carrying properties of a lubricant which is to be employed, for example, under extreme pressure conditions.

Recently, in an effort to obtain superior lubricants endowed with specific and superior characteristics, a new field has been exploded, namely the synthesis of lubricants from various materials. Esters represent one class of materials which have attracted unusual interest as synthetic lubricants. In general, they are characterized by higher viscosity indices and lower pour points than mineral oils of corresponding viscosity. The esters described in the present specification have been found to exhibit very low pour points and high viscosity indices. Lubricants possessing such properties are of special value in the lubrication of engines which are subjected to high temperatures, such as combustion turbine engines, particularly those of the "prop-jet" type. Mineral oil lubricants containing added viscosity index improvers, thickeners or other highly non-volatile additives are undesirable for use in such engines because of the tendency to leave a residue which accumulates and interferes with the operation of the engine. A synthetic lubricant of the type described in the present specification is especially adapted to use under such conditions, since the lubricant contains no additives and thus tends to leave no residue upon volatilization.

The new compounds of the present invention which have been found to be particularly suitable for use as lubricating oils are complex esters prepared by reacting one mol of a monohydric alcohol with one mol of a dibasic acid, thereby forming the half-ester of the dibasic acid, after which two mols of such half-ester are reacted with one mol of a glycol. The new class of compounds may be broadly defined by the following general formula:

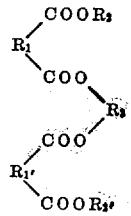

wherein $R_1$ and $R_1'$ are aliphatic hydrocarbon radicals, straight chain or branched, saturated or unsaturated, each containing 0 to 30 carbon atoms, or they may be organic radicals consisting of a series of saturated aliphatic hydrocarbon radicals interlinked by atoms of oxygen or sulfur, or both oxygen and sulfur, provided there are at least 2 carbon atoms between each pair of oxygen or sulfur atoms, and not more than 2 atoms of sulfur in each chain, and provided further that the total number of carbon, oxygen, and sulfur atoms in each radical is from 3 to 40. $R_2$ and $R_2'$ of the formula represent monohydric alcohol residues which may each be (1) a saturated straight chain aliphatic hydrocarbon radical containing not more than 5 carbon atoms, (2) a saturated branched chain hydrocarbon radical containing 3 to 20 carbon atoms, or (3) a series of saturated aliphatic hydrocarbon radicals, straight chain or branched, interlinked by oxygen or sulfur atoms, or both oxygen and sulfur atoms, the total number of carbon, oxygen, and sulfur atoms being from 4 to 20, and the number of oxygen or sulfur atoms or both in the radical being not more than 5. There should also be a chain of at least 2 carbon atoms between the acid radical and the first oxygen or sulfur atom and a similar chain of at least 2 carbon atoms between each pair of oxygen or sulfur atoms in the radical. $R_3$ of the formula represents a glycol radical, and it may consist of a saturated aliphatic hydrocarbon group, straight chain or branched, containing 2 to 20 carbon atoms, or it may be a series of saturated aliphatic hydrocarbon radicals interlinked by oxygen or sulfur atoms, or by both oxygen and sulfur atoms, provided there are at least 2 carbon atoms between each carboxyl group and the nearest oxygen or sulfur atom and at least 2 carbon atoms between each pair of oxygen or sulfur atoms in the chain. The total number of carbon, oxygen, and sulfur atoms in the entire $R_3$ radical is from 5 to 80 and the number of sulfur atoms is not greater than 2. To provide a product having sufficient viscosity for lubricating purposes the molecular weight of the entire ester should be at least 300, and to provide a product having a pour point sufficiently low, i. e., an A. S. T. M. pour point not higher than −10° F., it is generally necessary that the molecule contain at least 2 atoms of oxygen or sulfur, or both oxygen and sulfur, in ether or thioether linkages.

Among the various components of the complex esters of the present invention certain preferences may be pointed out as giving the optimum of desired properties from the standpoint of service as a lubricant. The preferred dibasic acids are the straight chain dibasic acids of the paraffinic group having from 6 to 10 carbon atoms per molecule. The preferred glycols are the polyethylene glycols of the formula $$HO(CH_2CH_2O)_nCH_2CH_2OH$$

where n is 1 to 26.

Illustrative examples of the dibasic acids which may be employed in the synthesis of the complex esters of the present invention are the following:

Oxalic acid
Malonic acid
Succinic acid
Glutaric acid
Adipic acid
Pimelic acid
Suberic acid
Azelaic acid
Sebacic acid
Brassylic acid
Pentadecanedicarboxylic acid
Tetracosanedicarboxylic acid
$C_4$–$C_{24}$ alkenylsuccinic acids
Diglycolic acid
Thiodigylcolic acid The $C_4$–$C_{24}$ alkenyl succinic acids listed above are prepared by condensing olefins or mixtures of olefins with maleic anhydride.

The monohydric alcohols employed are typified by the following:

Methyl alcohol
Ethyl alcohol
n-Butyl alcohol
2-ethylhexyl alcohol
Ethylene glycol mono-n-butyl ether
Ethylene glycol mono-2-ethylbutyl ether
Ethylene glycol mono-2-ethylhexyl ether
Ethylene glycol mono-tert.-octyl ether
β-n-Butylmercaptoethanol
β-Tert.-octylmercaptoethanol
β-n-Dodecylmercaptoethanol
Diethylene glycol mono-n-butyl ether
Diethylene glycol mono-2-ethylbutyl ether
Diethylene glycol mono-2-ethylhexyl ether
Propylene glycol mono-butyl thioether
Propylene glycol mono-tert.-octyl thioether
Propylene glycol mono-n-dodecyl thioether
n-Butylmercaptoethoxyethanol
Tert.-octylmercaptoethoxyethanol
n-Dodecylmercaptoethoxyethanol
n-Butylmercaptopropoxypropanol
Tert-octylmercaptopropoxypropanol
n-Dodecylmercaptopropoxypropanol
Propylene glycol mono-n-butyl ether
Dipropylene glycol monomethyl ether
Dipropylene glycol monoethyl ether
Dipropylene glycol mono-n-butyl ether
Tripropylene glycol monomethyl ether
Tripropylene glycol monoethyl ether
Tripropylene glycol mono-n-butyl ether
Propylene glycol monoisopropyl ether
Dipropylene glycol monoisopropyl ether
Tripropylene glycol monoisopropyl ether Many of the above listed ether alcohols, formed by the reaction of ethylene oxide or propylene oxide with aliphatic alcohols, are known in the industry as "Dowanols," "Carbitols," or "Cellosolves."

A group of alcohols especially adapted for use in the present invention are the so-called "Oxo" alcohols, prepared by the reaction of carbon monoxide and hydrogen upon the olefins obtainable from petroleum products. Materials such as diisobutylene and $C_7$ olefins are suitable for this purpose, also higher weight olefinic materials are sometimes employed. The alcohols obtained in this manner normally have a branched chain structure. The "Oxo" process for the preparation of alcohols was developed in Germany and first described in this country in Roelen U. S. Patent No. 2,327,066, granted August 17, 1943.

The glycols employed in preparing the esters of the present invention include ethylene glycol and any of the paraffinic homologues of the same containing up to 20 carbon atoms. These homologues may include, for example, propylene glycol, butylene glycols, pinacone, trimethylene glycol, tetramethylene glycol, pentamethylene glycol, and the like. Since the glycols may also contain oxygen or sulfur atoms, compounds such as diethylene glycol, triethylene glycol, the polyethylene glycols of the formula $$HO(CH_2CH_2O)_nCH_2CH_2OH$$

where n is 1 to 26, and the polypropylene glycols of the general formula $$HO(\overset{R}{\overset{|}{C}}H-\overset{R'}{\overset{|}{C}}HO)_nCH-CHOH$$

where R or R′ is a methyl group and the other is hydrogen and where n is 1 to 20, may likewise be employed. Glycols containing sulfur atoms in thioether linkages may also be employed, and these include such compounds as thiodiglycol and 1,2 - bis(2 - hydroxyethylmercapto)ethane. There also may be used glycols containing both oxygen and sulfur in similar linkages; such as a compound is bis-[2-(2-hydroxyethoxy)ethyl]sulfide.

It will be understood that when glycols are employed which contain no oxygen or sulfur in the chain, at least two such non-carbon atoms should be introduced into the molecule by means of the acid or monohydric alcohol employed in the esterification, since these non-carbon atoms are required for producing products of sufficiently low pour point, as stated above.

If desired, various addition agents may be incorporated in the esters of the present invention for the purpose of improving their properties with respect to their usefulness as lubricants. For example, antioxidants, viscosity index improvers, thickeners, pour depressants, dyes, etc., may be added.

Data will be given below showing the properties of several examples of complex esters within the scope of the present invention, indicating the adaptability of these esters to lubricating service. All of these esters were prepared by a general esterification method which may be described in detail as follows: In a 1-liter round bottom reaction flask, fitted with a reflux condenser and water trap, were placed 0.5 mol of dibasic acid, 0.5 mol of monohydric alcohol, 1.5 grams of p-toluene-sulfonic acid monohydrate (catalyst), and 100 ml. toluene. The mixture was refluxed until no more water collected in the water trap. After cooling, 0.25 mol of a glycol was added and the refluxing process resumed until again no more water collected in the trap. The mixture was washed with three 100-ml. portions of saturated aqueous sodium carbonate solution and one 100-ml. portion of water. After drying with "Drierite" (anhydrous calcium sulfate) the material was filtered and stripped at a pressure of about 12 mm. to a bath temperature of about 225° C.

The results of tests of various properties of esters prepared by the above general method are shown in the table of data which follows.

| Components of Ester | Flash point (° F.) | Kinematic Viscosity | | ASTM Slope | Viscosity Index | ASTM Pour Point (° F.) |
|---|---|---|---|---|---|---|
| | | 100° F. | 210° F. | | | |
| Adipic acid<br>n-Butyl alcohol<br>Trimethylene glycol | 390 | 38.730 | 7.704 | 0.605 | 152 | −10 |
| Adipic acid<br>n-Butyl alcohol<br>Triethylene glycol | 405 | 58.170 | 10.400 | 0.585 | 146 | <−35 |
| Adipic acid<br>$C_8$ "Oxo" alcohol<br>Triethylene glycol | 425 | 36.490 | 7.272 | 0.619 | 151 | <−35 |
| Adipic acid<br>$C_8$ "Oxo" alcohol<br>Tetraethylene glycol | 435 | 46.039 | 8.728 | 0.598 | 149 | <−35 |
| Adipic acid<br>Ethylene glycol monoethyl ether<br>Thiodiglycol | 385 | 25.010 | 5.338 | 0.662 | 155 | <−35 |
| Adipic acid<br>Dipropylene glycol monoisopropyl ether<br>Tetraethylene glycol | 435 | 66.658 | 11.115 | 0.592 | 141 | <−35 |
| Adipic acid<br>$C_{10}$ "Oxo" alcohol<br>Tetraethylene glycol | 455 | 48.943 | 8.989 | 0.602 | 146 | <−35 |
| Sebacic acid<br>2-ethylhexanol<br>Tetraethylene glycol | 470 | 66.758 | 12.327 | 0.549 | 148 | <−35 |
| Sebacic acid<br>$C_8$ "Oxo" alcohol<br>Tetraethylene glycol | 480 | 66.858 | 12.379 | 0.547 | 148 | <−35 |
| Sebacic acid<br>$C_8$ "Oxo" alcohol<br>Triethylene glycol | 455 | 48.800 | 9.541 | 0.574 | 152 | −10 |
| $C_{14}$–$C_{18}$ alkenyl succinic acid*<br>Methyl alcohol<br>Triethylene glycol | 485 | 245.3 | 20.650 | 0.648 | 105 | −10 |
| Oxalic acid<br>$C_8$ "Oxo" alcohol<br>Tetraethylene glycol | 420 | 37.240 | 6.407 | 0.688 | 130 | <−35 |
| Thiodipropionic acid<br>n-Butyl alcohol<br>Trimethylene glycol | 385 | 24.710 | 5.287 | 0.663 | 155 | <−35 |

*Prepared by condensing a $C_{14}$–$C_{18}$ olefin mixture with maleic anhydride.

The above data indicate that the esters constituting the subject matter of the present invention possess characteristics, particularly with regard to viscosity index and pour point, which indicate their suitability for general use as lubricating oils and particularly for use where the utilization of additives is not desirable. The esters of the present invention may also be blended with mineral lubricating oils to give lubricants of improved viscosity index and pour point.

What is claimed is:

1. As a new composition of matter, a compound of the formula $$R_2OOCR_1COOR_3OOCR_1'COOR_2'$$

wherein $R_1$ and $R_1'$ are straight chain aliphatic hydrocarbon groups each containing from 0 to 8 carbon atoms, wherein $R_2$ and $R_2'$ are branched chain aliphatic hydrocarbon groups containing from 4 to 20 carbon atoms each, at least one of said groups containing at least one atom of the group of oxygen and sulfur in ether linkage, and wherein $R_3$ is a radical of the formula $$—(CH_2CH_2O)_nCH_2CH_2—$$

wherein n is a number of from 1 to 26, the components of the composition being so chosen that the molecular weight thereof is at least 300.

2. A composition according to claim 1 wherein $R_1$ and $R_1'$ contain from 7 to 8 carbon atoms and wherein n is from 3 to 8.

[3. A composition according to claim 1 wherein $R_2$ and $R_2'$ are derived from ethylene glycol monoethyl ether.]

4. A composition according to claim 1 wherein $R_2$ and $R_2'$ are derived from dipropylene glycol monoisopropyl ether.

5. As a new composition of matter, a compound of the formula $$R_2OOC(CH_2)_xCOO(CH_2CH_2O)_nOC(CH_2)_xCOOR_2$$

wherein $R_2$ is a branched chain aliphatic hydrocarbon radical of from 4 to 13 carbon atoms, wherein x is a number of from 7 to 8, and wherein n is a number of from 3 to 8.

6. A compound according to claim 5 wherein $R_2$ contains about 8 carbon atoms.

7. A compound according to claim 5 wherein x is about 8.

8. A compound according to claim 5 wherein n is about 4.

9. As a new composition of matter, a compound of the formula $$C_8H_{17}OOC(CH_2)_8COO(CH_2CH_2O)_4OC(CH_2)_8COOH_{17}C_8$$

References Cited in the file of this patent or the original patent

UNITED STATES PATENTS

| | | |
|---|---|---|
| 2,023,485 | Malm | Dec. 10, 1935 |
| 2,075,107 | Frazier | Mar. 30, 1937 |
| 2,295,165 | De Groote | Sept. 8, 1942 |
| 2,363,045 | De Groote | Nov. 21, 1944 |
| 2,375,529 | De Groote | May 8, 1945 |
| 2,379,251 | Muskat | June 26, 1945 |
| 2,392,621 | Strain | Jan. 8, 1946 |
| 2,415,366 | Muskat | Feb. 4, 1947 |
| 2,628,974 | Sanderson | Feb. 17, 1953 |
| 2,668,848 | Neuworth | Feb. 9, 1954 |